United States Patent [19]

Dahn

[11] 4,233,835
[45] Nov. 18, 1980

[54] ELECTROSTATIC DISCHARGE TESTER

[75] Inventor: C. James Dahn, Chicago, Ill.

[73] Assignee: Safety Consulting Engineers Inc., Rosemont, Ill.

[21] Appl. No.: 32,699

[22] Filed: Apr. 23, 1979

[51] Int. Cl.³ .............................................. G01N 33/22
[52] U.S. Cl. ........................................ 73/35; 324/452
[58] Field of Search ................... 73/35; 324/61 R, 54, 324/32, 452

[56] References Cited

U.S. PATENT DOCUMENTS

| | | |
|---|---|---|
| 1,506,761 | 9/1924 | MacPherson .......................... 324/54 |
| 1,997,064 | 4/1935 | Lusignan ............................ 324/54 X |
| 2,836,792 | 5/1958 | Weber ................................. 324/61 R |
| 2,869,364 | 1/1959 | Kabik et al. ......................... 73/35 X |
| 3,760,262 | 9/1973 | Chovanec et al. ................... 73/35 X |
| 3,975,942 | 8/1976 | Dreitzler et al. ....................... 73/35 |

*Primary Examiner*—James J. Gill
*Attorney, Agent, or Firm*—Rummler & Snow

[57] ABSTRACT

A testing apparatus for determining and evaluating the sensitivity of propellants and other hazardous materials to electrostatic discharges carried and stored on apparatus or individuals by simulating and controlling their normal force by being exposed to an electrical discharge.

8 Claims, 3 Drawing Figures

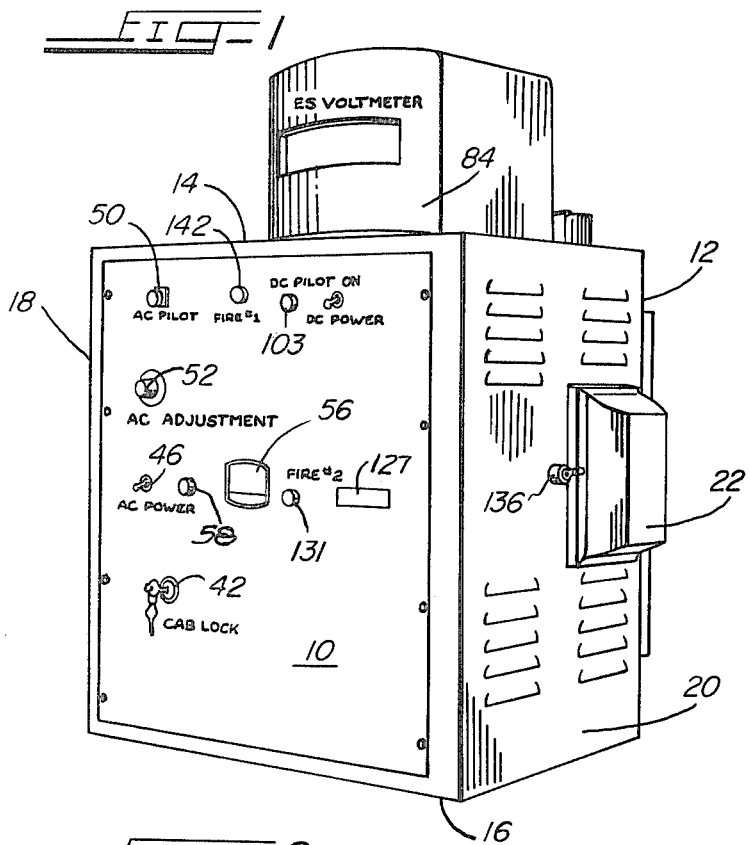
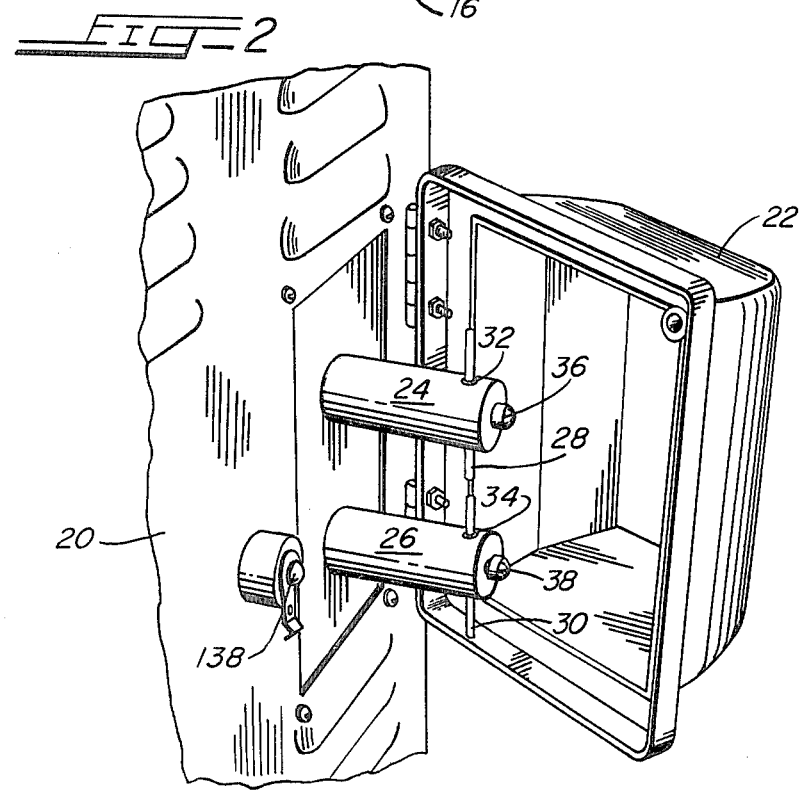

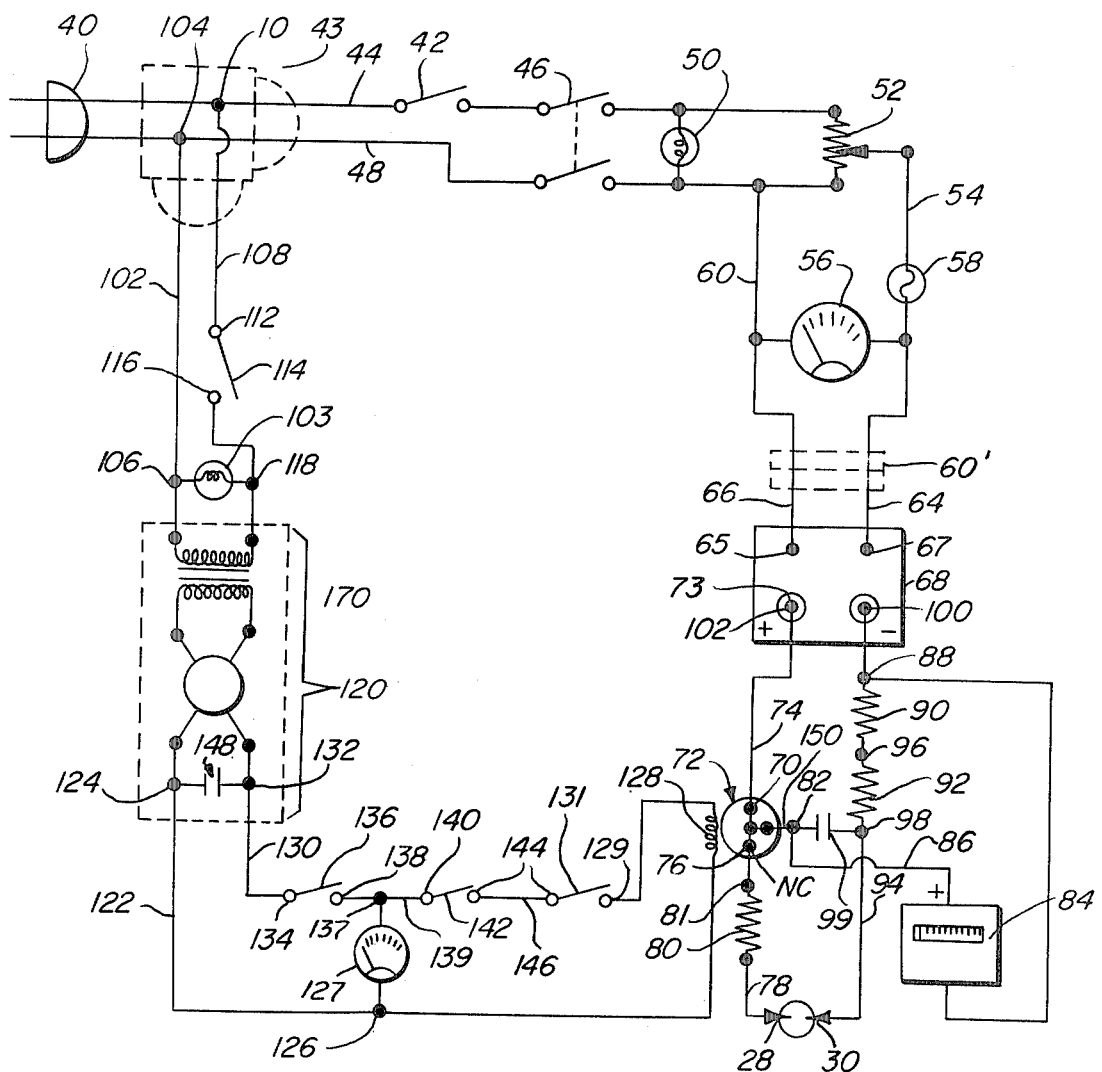

4,233,835

ELECTROSTATIC DISCHARGE TESTER

BACKGROUND OF THE INVENTION

1. Field of the Invention

This invention relates to testing apparatus and more particularly to an electrostatic discharge tester for use in determining and evaluating the sensitivity of propellants and other hazardous materials to electrostatic discharges.

2. Description of the Prior Art

Most propellants are highly volatile in nature and may be ignited due to discharge of an electrostatic charge carried and stored on apparatus, with which the propellant is used, or by an individual moving in the proximity. Testing of samples of the propellant prior to its use is important to determine its susceptibility to electrostatic discharge to aid in designing the environment in which the material is used as well as in establishing guidelines for handling of the material.

SUMMARY OF THE INVENTION

The present invention provides an electrostatic discharge tester for use in determining and evaluating the sensitivity of materials to electrostatic discharges by controlling their normal force. The test apparatus is designed to ignite propellants or other hazardous materials by subjecting the test sample to an electrical discharge. The test results indicate conditions for which the test sample will ignite with and without moisture when exposed to an electrical current.

The testing apparatus comprises electrical circuitry which is effective to generate an electrical discharge in the proximity of a test sample during testing of the sample. During a testing procedure, a test sample in powder form is placed within a piece of plastic tubing which is then centered on a pair of spaced spark electrodes with the powder sample located in the spark gap. The electrical circuits are then activated and through capacitive discharge, a high voltage, in the order of 30 KVDC, is applied to the electrodes generating a high energy spark in the spark gap. The color of the spark indicates whether or not the powder has ignited in response to the spark. For example, if there is no reaction, the color of the spark is blue. For a partial reaction, the spark is colored orange, and if the plastic sample tube is fractured, then the sample has fired.

During a testing operation, capacitors of different values are used during different stages of the test operation in determining the susceptibility of the powder sample to ignition under exposure to electrical discharge of higher and lower energy levels.

In accordance with a feature of the invention, the test sample and the spark electrodes are enclosed within a transparent cover member which affords viewing of the test sample during testing.

BRIEF DESCRIPTION OF THE DRAWINGS

FIG. 1 is a perspective view of the cabinet, the electrostatic volt meter and the housing for the electrodes;

FIG. 2 is a perspective view of electrodes and cover therefor mounted on the side wall of the cabinet; and FIG. 3 is a circuit diagram for the test apparatus of the present invention.

DESCRIPTION OF THE PREFERRED EMBODIMENT

Referring to FIG. 1 of the drawings, the cabinet houses electrical circuitry which is effective to generate an electrical discharge during testing of a sample. During a testing procedure, the sample is positioned in a sample chamber defined by a transparent shield 22 which is pivotally hinged to one side of the cabinet.

Referring to FIG. 2, the sample (not shown) under test is mounted in the proximity of a pair of spark electrodes 28 and 30. The test sample, in powder form, is placed within a piece of plastic tubing (not shown) which is centered on the electrodes 28 and 30 with the powder sample located in the gap between the electrodes. The electrical circuits are then activated in a manner to be described, and a high voltage, in the order of 30 KVDC, is applied to the electrodes 28 and 30, generating a high energy spark in the spark gap. The color of the spark indicates whether or not the powder has ignited in response to the spark. For example, if there is no reaction, the color of the spark is blue. For a partial reaction, the spark is colored orange, and if the plastic sample tube is fractured, then the sample has fired.

Referring to FIG. 3, the electrical circuits include a capacitive discharge circuit comprised of a capacitor 99 which is initially charged and then discharged over the spark electrodes 28 and 30 in response to operation of a relay 72. During a testing operation, capacitors of different values, such as 0.01 MFD, 0.005 MFD, 0.02 MFD, are used during stages of the test operations in determining the susceptibility of the test sample to ignition under exposure to electrical discharges of various and lower energy levels.

For the purpose of charging the capacitor 99, the spark producing circuit further includes a high voltage transformer 68 which supplies a high voltage DC to the capacitor 99. An electrostatic voltmeter 84 indicates the charge on the capacitor 99. The high voltage transformer 68 has its primary connected to a source of AC voltage via line switches 42 and 46, when the switches are closed. The amplitude of the AC voltage applied to the HV primary is adjustable by way of rheostat 52. A meter 56 indicates the applied AC voltage.

Capacitor 99 is connected in a charging circuit with resistors 92 and 90 across the output of the high voltage transformer 68 by way of normally closed contacts of a relay 72. The relay is operated under the control of an actuating circuit, comprised of AC to DC converter 120 and operating switches 131 and 142, to connect the capacitor 99 and discharge resistance 80 across the electrodes 28 and 30 permitting the capacitor to discharge and generate a spark in the gap between the electrodes. A power switch 114 permits energization of the actuating circuit independently of the spark generating circuit. A meter 127 indicates the amplitude of the DC voltage provided by the power circuit 170.

Referring to FIG. 1, the housing comprises control panel 10, a rear panel 12, a top panel 14, a bottom panel 16 and side panels 18 and 20. The interior of the cabinet is interiorly insulated.

The control panel 10 mounts the operating switches 42, 46, 114, 131 and 142, the meters 56 and 127, and pilot lights 50 and 103 of the electric circuits. Switch 42 is a key operated switch which is connected to the main power line as shown in FIG. 3. Switch 46 is the AC power switch which extends AC power to the spark generating circuit. Meter 56 monitors the AC voltage applied to the primary of the high voltage transformer 68. The electrostatic volt meter which measures the charge on the capacitor 99 is mounted on the top of the cabinet.

Switch 114 is the power switch for the relay actuating circuit which extends AC power to the AC to DC converter 120 of the relay actuating circuit. Meter 127 monitors the applied voltage for the actuating circuit. Switches 131 and 142 are "fire" switches which enable the user to operate the relay 72 and connect the capacitor across the spark electrodes during a testing operation. A further switch 136, which is mounted adjacent to the sample compartment, is a door switch which is maintained closed when the transparent shield is in the closed position. Whenever the shield 22 is in the open position, the switch 136 interrupts the DC supply to the relay, preventing its operation.

The clear plastic shield 22, which is preferably plexiglass, is hingedly mounted on side wall 20. The shield houses a pair of spaced electrode holders 24 and 26 which support the electrodes 28 and 30 shiftable transversely of the electrode holders in apertures 32 and 34. Threadedly mounted screws 36 and 38 are positioned axially in the holders 24 and 26 at the free ends thereof to support the electrodes and for spacing the gap between them at one end thereof.

Referring to FIG. 3, AC power is supplied to the circuits by way of a power cord having an electrical plug 40 for insertion into an electrical outlet. The power cord extends AC current through a junction box 43 to key switch 42, which is connected in line 44 on one side of the line 44. The key switch 42 controls the current flowing through the circuit.

The main, normally open power switch 46 is a double-pole switch with contacts connected in both lines 44 and 48 to make certain there is no residual current in the circuit. Switch 46 is shown physically in FIG. 1 as the toggle switch on the front panel 10. An AC pilot light 50, which is connected behind the switch, is lit whenever AC current is flowing through lines 44 and 48. The variable rheostat 52, which is connected between lines 44 and 48, permits adjustment of the AC voltage supplied to the spark generating circuit.

The tap on the rheostat is connected in line 54 to one side of voltmeter 56, which is a 0 to 150 volt AC voltmeter, and a fuse 58 is connected therebetween. The other side of the voltmeter 56 is connected to line 48 through line 60. The lines 54 and 60 are connected to inputs of a junction box 60' having lines 64 and 66 which are connected to taps 65 and 67 on one primary side of the high voltage transformer 68. The transformer output is in the order of 30 KV direct current for an input of approximately 100 VAC. The positive terminal 73 of the HV secondary of the transformer 68 is connected through line 74 to a normally closed contact 70 of relay 72, which is a vacuum relay. A normally open contact 76 is connected to the electrode 28 in line 78. A resistor 80 is connected to the junction 81 in line 78 and to the spark electrode 28. A second normally closed contact 82 is connected to the positive terminal of the electrostatic voltmeter 84 through line 86, which has its negative terminal connected to the negative terminal 100 to the HV secondary. Junction 98 in line 94 is connected to junction 82, as well as to electrode 30. The capacitor 99 is connected between junctions 82 and 98.

Referring to the relay actuating circuit, line 102 is connected to one side of a pilot light 103 between junctions 104 in lines 48 and 106. Line 108 is connected between junction 110 in line 44 and one side 112 of normally open switch 114. The other terminal 116 of switch 114 is connected to the opposite side of the DC supply pilot light at junction 118.

Lines 102 and 104 are connected to the upper end of the 24 volt DC power supply 120. Line 122 is connected to junction 124 and to junction 126 and to one side of coil 128 of the vacuum relay and thence back to the open side of fire switch #2 (numeral 131). The 0-50 direct current voltmeter 127 is connected between junctions 126 and 131. Line 130 connects between junction 132 and one side 134 of the normally open door switch 136. The open side of the switch 138 is connected to one side 140 of normally open fire switch 142 through line 139. The opposite side 144 is connected to junction 144 of switch 131 through line 146. A filter capacitor 148 is connected between junctions 124, 132.

When a 110 AC voltage is connected to the high voltage DC transformer 68, up to 3000 volts of DC power is developed at the output of the transformer 68. The DC voltage is adjustable by use of variable transformers on the alternating current side. This high voltage is applied to the capacitor 99 for charging the capacitor. When the relay 72 is subsequently operated, the capacitor is discharged over the spark electrodes and the test sample.

The energy which comes out of the system is a function of capacitance voltage:

$E = \frac{1}{2} CV^2$

Joules $= \frac{1}{2}$ (mfd) (KV)

In one tester unit, three interchangeable capacitors, i.e., 0.005 mfd, 0.01 mfd, or 0.02 mfd, were used, and with suitable choice of applied DC, the resultant energy was 2.25 Joules, 4.50 Joules and 9.00 Joules respectively.

Although not shown in the drawings, the charging capacitor 99 and vacuum relay 72 are insulatively mounted on a platform above the bottom panel 16. A metal screen is employed interiorly of the housing for shielding the high voltage components from the control components.

Operation

The first step is to prepare pieces of plastic tubing (not shown) is preferably $\frac{3}{4}$ inch lengths and having an internal diameter of a fraction of an inch larger than the outside diameter of the electrode. After thoroughly cleaning the tubing, the powdered sample to be tested is placed interiorly of the tube and is preferably one-tenth of an inch in thickness, plus or minus one one-hundredths of an inch.

Then, after grounding both of the electrodes 28 and 30, one end of the tube is placed on the lower electrode 30 after the removal of the other electrode. The upper electrode 28 is then repositioned in the electrode holder and the end inserted interiorly of the tube. The electrodes are closed together with the powder therebetween at a gap thickness in the order of 0.1 of an inch. The tube is then centered on the electrodes. Then the electrodes are firmly positioned by tightening the mounting screws 36, 38. The shield 22 is then closed, as in FIG. 1, and latched tight by latch switch 136.

The power cord is then plugged into an alternating current outlet and the key switch 42 closed.

With AC power applied to the spark generating circuit, the rheostat 52 is adjusted to zero, or minimum resistance. Then the electrostatic voltmeter 84 is adjusted to set it at its highest volt reading on the upper scale thereof. The power switch 46 is then operated on and the pilot light 50 is noted to be certain it glows. The AC voltage is adjusted to zero while viewing the AC meter 56.

Then, while viewing meter 56, the AC voltage is carefully and slowly adjusted by operating rheostat 52 until the desired high DV voltage (less than 30 KVDC) is applied to the capacitor 99. The capacitor used for the first stage testing is OF 300-103$^2$ sp. 0.01 Mfd 30 KV DC.

The power switch 114 is closed energizing the relay actuating circuit, and the DC voltmeter 127 is read to assure that sufficient DC voltage is available for the relay 72.

After the unit has been calibrated following the above procedure, the user operates both fire switches 131 and 142 simultaneously, while viewing the sample in the compartment to note the color of the spark. If the spark is colored blue, there was no reaction. If the spark is colored orange, there was a partial reaction. If the plastic sample has been fractured, then it should be noted as having been fired. If not, then the record should note the test as no-fire. After the first arc between the electrodes 30, 32 is flashed, the switches 131 and 142 are released.

After the first test, the Bruceton up and down procedure is recommended. Thus, if the first test results in a "Fire", for the next test stage a capacitor of a size of OF-300-502$^2$ sp. 0.005 Mfd 30 KV DC is substituted for the one used and a new sample is inserted into the test chamber. If, on the other hand, the first test results in "No Fire", then the capacitor OF-300-203$^3$ sp. 0.02 Mfd 30 KV DC is used for the next test.

Although but one specific embodiment of this invention is herein shown and described, it will be understood that details of the construction shown may be altered or omitted without departing from the spirit of the invention as defined by the following claims.

I claim:

1. A test apparatus for determining the sensitivity of a substance to electrostatic discharge, comprising:
   ignition electrode means including a pair of elongated generally cylindrical spark electrodes, and means for mounting said spart electrodes with respective end portions disposed in a spaced relationship defining a spark gap therebetween;
   activate means including output circuit means for storing electrical energy and energizing means for supplying energy to said output circuit means;
   actuating means including switching means operable when enabled to connect said output circuit means to said spark electrodes to transfer the energy stored by said output circuit means to said electrodes whereby a high energy spark is generated in the gap between said electrodes;
   and support means for positioning a sample of the substance adjacent to said spark electrodes to permit the sample to be subjected to the high energy spark generated in the gap,
   said support means comprising a hollow tubular member having an internal diameter of a fraction of an inch larger than the outside diameters of said electrodes, permitting the tubular member to be mounted on said electrodes with the end portion of one electrode extending through one end of the tubular member and the end portion of the other electrode extending through the opposite end of said tubular member whereby said tubular member is supported by said electrodes with said end portions of said electrodes extending axially therewithin, and said sample being contained within said tubular member and positioned in the spark gap between said electrodes.

2. Apparatus according to claim 1 including an enclosure means, said electrode mounting means being supported within said enclosure means and said enclosure means having a transparent cover member for exposing said electrodes to view, said cover member being mounted for movement to an open position providing access to said electrodes for mounting a sample thereupon.

3. Apparatus according to claim 1 wherein said output circuit means comprises a capacitor and resistance means, said switching means normally connecting said capacitor and said resistance means to outputs of said energizing means for charging said capacitor, and said switching means being operable when energized to connect said capacitor in circuit with said spark electrodes, permitting said capacitor to discharge thereover whereby the energy stored in said capacitor is transferred to the spark gap for generating a spark at the location of the sample.

4. Apparatus according to claim 1 which includes means for measuring the energy stored by said output circuit means prior to operation of said switching means.

5. Apparatus according to claim 1 which further comprises input means for supplying an AC power signal to said activate means, and adjustable means for adjusting the amplitude of the AC power signal supplied to said activate means to thereby control the amount of energy stored by said output circuit means.

6. Apparatus according to claim 5 wherein said actuating means further comprises converter means for deriving an enabling signal for said switching means from the AC power signal, and switch means manually operable to extend said enabling signal to said switching means for enabling said switching means.

7. A test apparatus for determining the sensitivity of a substance to electrostatic discharge, comprising:
   ignition electrode means including a pair of spark electrodes, and means for mounting said spark electrodes with respective end portions disposed in a spaced relationship defining a spark gap therebetween;
   enclosure means, said electrode mounting means being supported within said enclosure means;
   activate means including output circuit means for storing electrical energy and energizing means for supplying energy to said output circuit means;
   actuating means including switching means operable when enabled to connect said output circuit means to said spark electrodes to transfer the energy stored by said output circuit means to said electrodes whereby a high energy spark is generated in the gap between said electrodes;
   support means for positioning a sample of the substance adjacent to said spark electrodes to permit the sample to be subjected to the high energy spark generated in the gap, said support means including a hollow tubular member mountable on and supported by said electrodes with said end portions of said electrodes extending axially therewithin, and said sample being contained within said tubular member and positioned in the spark gap between said electrodes;

said enclosure means having a transparent cover member for exposing said electrodes to view, said cover member being mounted for movement to an open position providing access to said electrodes for mounting said tubular member thereupon, and safety switch means associated with said cover member and operated to inhibit said switching means, preventing operation thereof whenever said cover is at its open position.

8. A test apparatus for determining the sensitivity of a substance to electrostatic discharge, comprising:

ignition electrode means including a pair of elongated generally cylindrical spark electrodes and means for mounting said electrodes with respective end portions disposed in a spaced relationship defining a spark gap therebetween;

high voltage DC source means;

input means for activating said DC source means;

energy storage means including a capacitor and resistance means connected in circuit with said capacitor between outputs of said DC source means for supplying energy to said capacitor in response to activation of said DC source means;

actuating means including switching means operable when enabled to connect said capacitor in circuit with said spark electrodes to transfer the energy stored on capacitor to said electrodes generating a high energy spark in the spark gap; and support means for positioning said test sample in the gap between said electrodes to permit the sample to be subjected to the high energy spark generated in the gap, said support means comprising a hollow tubular member having an internal diameter of a fraction of an inch larger than the outside diameters of said electrodes, permitting the tubular member to be mounted on said electrodes with the end portion of one electrode extending through one end of the tubular member and the end portion of the other electrode extending through the opposite end of said tubular member whereby said tubular member is supported by said electrodes with said end portions of said electrodes extending axially therewithin, and said sample being contained within said tubular member and positioned in the spark gap between said electrodes.

* * * * *